(12) United States Patent
Deshpande et al.

(10) Patent No.: US 7,993,922 B2
(45) Date of Patent: Aug. 9, 2011

(54) THREE-DIMENSIONAL TISSUE EQUIVALENT USING MACROMASS CULTURE

(75) Inventors: Manisha Sharadchandra Deshpande, Maharashtra (IN); Sithamraju Harinarayana Rao, Maharashtra (IN); Pralhad Balasaheb Wangikar, Maharashtra (IN); Pushpa Vikram Kuchroo, Maharashtra (IN)

(73) Assignee: Reliance Life Sciences Pvt. Ltd., Maharashtra (IN)

(*) Notice: Subject to any disclaimer, the term of this patent is extended or adjusted under 35 U.S.C. 154(b) by 378 days.

(21) Appl. No.: 11/976,960

(22) Filed: Oct. 30, 2007

(65) Prior Publication Data
US 2008/0145344 A1 Jun. 19, 2008

Related U.S. Application Data

(63) Continuation-in-part of application No. 10/686,822, filed on Oct. 16, 2003, now abandoned.

(30) Foreign Application Priority Data

Oct. 18, 2002 (IN) ............................ 912/MUM/2002

(51) Int. Cl.
*C12N 5/07* (2010.01)
*C12N 5/00* (2006.01)
(52) U.S. Cl. ...................... 435/395; 435/402; 424/93.7
(58) Field of Classification Search .................. None
See application file for complete search history.

(56) References Cited

U.S. PATENT DOCUMENTS

| | | | |
|---|---|---|---|
| 5,273,900 A | 12/1993 | Boyce | |
| 5,755,814 A | 5/1998 | Berg et al. | |
| 6,197,586 B1 | 3/2001 | Bhatnagar et al. | |
| 6,645,489 B2 | 11/2003 | Pykett et al. | |
| 6,699,287 B2 * | 3/2004 | Son et al. .................. | 623/15.12 |
| 7,192,769 B2 | 3/2007 | Pykett et al. | |

FOREIGN PATENT DOCUMENTS

| WO | WO 01/91821 | 12/2001 |
|---|---|---|
| WO | WO-2005/095585 A1 | 10/2005 |

OTHER PUBLICATIONS

Yan et al. "Chitosan-alginate films prepared with chitosans of different molecular weights". J. Biomed. Mater. Res. (Appl Biomater), 2001, 58:358-365.*
Mao et al. "Study of novel chitosan-gelatin artificial skin in vitro". J. Biomed. Mater. Res. 2003, 64A: 301-308.*
Chauhan et al.; "Nonhealing Wounds—Therapeutic Dilemma"; Lower Extremity Wounds; 2003; 2:40-45.
Eisenbud et al.; "Skin Substitutes and Wounds Healing: Current Status and Challenges"; Wounds; 2004; 6:2-17.
Marston et al.; "The Efficacy and Safety of Dermagraft in Improving the Healing of Chronic Diabetic Foot Ulcers"; Diabetes Care; 2003; 26:1701-1705.
Montesano et al.; "Transforming growth factor β stimulates collagen-matrix contraction by fibroblasts: Implications for wound healing"; Proc. Natl. Acad. Sci.; 1988; 85:4894-4897.
Green et al.; "Growth of cultured human epidermal cells into multiple epithelia suitable for grafting"; Proc. Natl. Acad. Sci.; 1979; 76:5665-5668.
Khor et al.; "Preliminary study of a polycaprolactone membrance utilized as epidermal substrate"; J. Mater Sci Mater. Med.; 2003; 14(2):113-120.
Imaizumi et al.; "Cultured Mucosal Cell Sheet with a Double Layer of Keratinocytes and Fibroblasts on a Collagen Membrane"; Tissue Eng. 2004; 105(5-6):657-664.
Yang et al. ; "Fabrication and surface modification of macroporous poly($_L$-lactic acid) and poly($_L$-lactic-$co$-glycolic acid) (70/30) cell scaffolds for human skin fibroblast cell culture"; J. Biomed. Mater. Res.; 62(3):438-446, (2002).
Di Stefano et al.; "Angiogenesi terapeutica nell'ischemia criteria degli arti inferiori. Revisione della letteratura e prospettive della ricerca sulle cellule staminali"; Ital. Heart. J.; 2004; 5:1-13.
Feugate et al.; "The cxc chemokine cCAF stimulates differentiation of fibroblast into myofibroblast and accelerates wound closures"; 2002; J. Cell Biol. 2002; 156:161-172.
J. Bryan, "Moist wound healing: a concept that changed our practice"; J. Wound Care; 2004; 13:227-228.
M. Deshpande; "Three-dimensional organization of dermal fibroblasts by macromass culture"; Biotechnol. 2007; Jul. 11, PMID:17623015, DOI:10.1042/BA20070120.
Shi et al.; "Therapeutic Potential of Chitosan and Its Derivatives in Regenerative Medicine"; J. Surg. Res.; 2006; 133:185-192.
Bach; "Toward an understanding of the basis of alloantigen recognition"; Immunol Lett 1989; 21(1):21-24.
Ferrara et al.; "The biology of VEGF and its receptors"; Nature Med.; 2003; 9(6):669-676.
Mansbridge et al.; "Growth factors secreted by fibroblasts: role in healing diabetic foot ulcers"I Diabetes Obes. Metab.; 1999; 1(5):265-279.
Martin et al.; "Effects of human fibroblast-derived dermis on expansion of tissue from venous let ulcers"; Wound Rep. Reg. 2003; 11(4):292-296.
Liu, et al.; "Mechanism of Action of Camptothecin"; Ann. N.Y. Acad. Sci.; 2000; 922:1-10.
Falanga, V. Advanced Treatments Chronic Wounds; Apr. 2005; http://www.worldwidewounds.com/2005/april/Falanga/Advanced-Treatments-Chronic-Wounds.html Feb. 2006.
Rosenberg et al.; "Wound Healing, Growth Factors" EMedicine.com http://www.emedicine.com/plastic/topic457.htm Jun. 2006.
Thuesen, The University of Montana SPAHS Drug Information Service, No. 5, pp. 1-3 (2001).

(Continued)

*Primary Examiner* — Vera Afremova
(74) *Attorney, Agent, or Firm* — Foley & Lardner LLP

(57) ABSTRACT

The present invention provides a three-dimensional tissue equivalent for in-vivo and in-vitro uses. The three dimensional tissue equivalent of the present invention is a non-contractile cellular sheet cultured over a porous scaffold using a macromass culturing technique, for example where the cellular sheet is entirely on one side of a porous sponge. In one embodiment, the present invention provides a dermal wound dressing that comprises a high density cellular sheet of dermal fibroblast cells.

7 Claims, 9 Drawing Sheets

OTHER PUBLICATIONS

Lee et al., "Study of Gelatin-Containing Artificial Skin V: Fabrication of Gelatin Scaffolds Using a Salt-Leaching Method," *Biomaterials*, pp. 1961-1968 (2005).

Atiyeh et al., New Technologies for Burn Wound Closure and Healing-Review of the Literature, *Burns*, pp. 944-956 (2005).

Ahrens et al., "Stage-Related Capacity for Limb Chondrogenesis in Cell Culture," *Developmental Biology*, vol. 60, pp. 69-82 (1977).

Furukawa et al., "Formation of Human Fibroblast Aggregates (Spheroids) by Rotational Culture," *Cell Transplantation*, vol. 10, pp. 441-445 (2001).

* cited by examiner

Fig. 1A
Fig. 1B
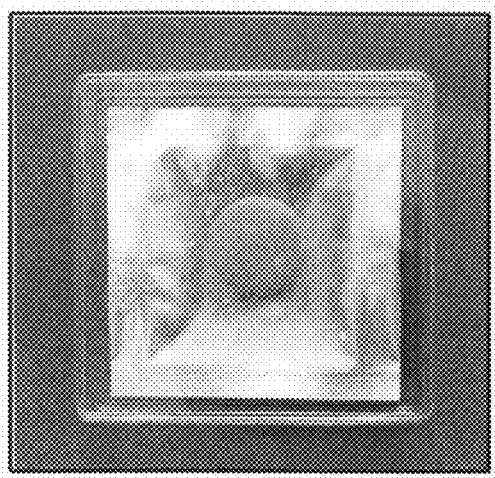
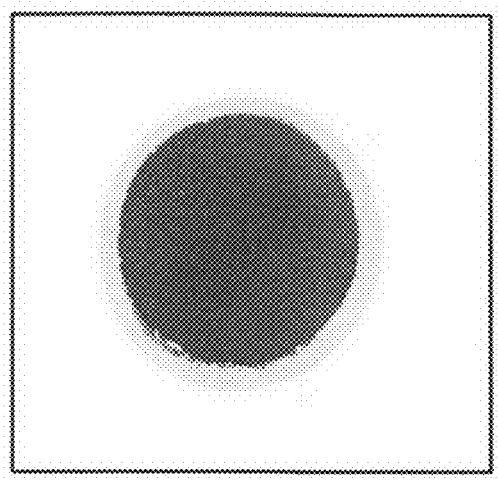
Fig. 2
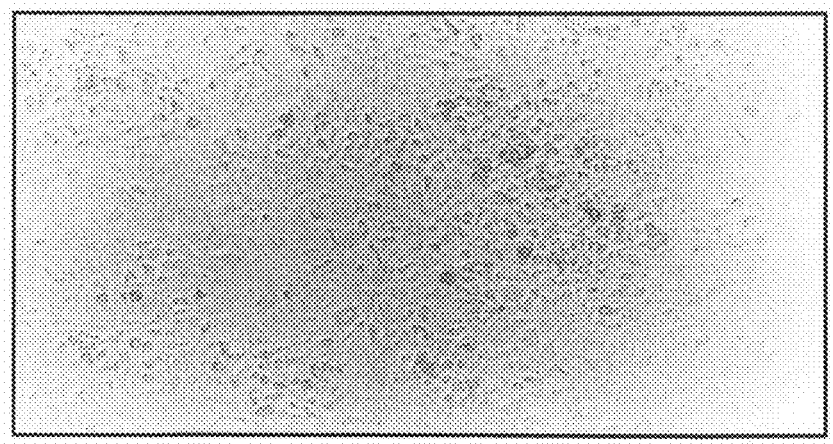

1. Marker
2. Batch 1 spent transport medium
3. Batch 2 spent transport medium
4. Batch 3 spent transport medium
5. Batch 1 first wash
6. Batch 2 first wash
7. Batch 3 first wash
8. Fetal bovine serum Monolayers of Fibroblasts 1. Without tissue equivalent of the present invention.
2. With tissue equivalent of the present invention.

Toxicity Testing of Camptothecin

THREE-DIMENSIONAL TISSUE EQUIVALENT USING MACROMASS CULTURE

CROSS REFERENCE TO RELATED APPLICATIONS

This application is a continuation-in-part of U.S. patent application Ser. No. 10/686,822, filed Oct. 16, 2003, which claims the benefit of India application Ser. No. 912/MUM/2002, filed Oct. 18, 2002, now Indian Patent No. 195953, all of which are hereby incorporated by reference in their entirety for all purposes. Related applications, India application Ser. Nos. 2013/MUM/2006 and 2014/MUM/2006, were also filed in India on Dec. 8, 2006.

FIELD OF THE INVENTION

The present invention relates to the field of tissue engineering for in vivo or in vitro uses. The present invention further relates to a non-contractile three-dimensional tissue equivalent as a dermal wound dressing and its methods of preparation. The present invention also relates to therapeutic applications of the non-contractile three-dimensional tissue equivalent and its safety and efficacy evaluation in the treatment of wounds. Alternatively the three-dimensional tissue equivalent of the present invention can also be used for in vitro cytotoxicity screening of compounds.

BACKGROUND OF THE INVENTION

Skin Dermis

Dermal fibroblasts are cells present in the extracellular matrix within the dermis of the skin. The dermis provides strength and flexibility to the skin and is also a supporting structure for blood vessels, the lymphatic system, nerves, sweat glands and hair follicles. Fibroblasts are the major cell type of the dermis, producing and maintaining the extracellular matrix, which in turn supports other cell types. See Parenteau et al. (2000) "Skin." *Principles of Tissue Engineering*. 2$^{nd}$ Ed. Academic Press, San Diego. Fibroblasts secrete various growth factors and cytokines, and produce new extracellular matrix in the granulation tissue. When a wound in the dermis develops, fibroblasts are converted to a contractile myofibroblast phenotype, which initiates wound contraction and epithelization, and leads to complete wound closure.

Etiology of Wounds

Wound healing, or wound repair, is the body's natural process of regenerating dermal and epidermal tissue. When an individual is wounded, a set of events takes place in a predictable fashion to repair the damage. These events overlap in time and must be artificially categorized into separate phases: the inflammatory, proliferative, and maturation phases. See Clark et al. (2000) "Wound repair: Basic Biology to Tissue Engineering." *Principles of Tissue Engineering*. 2$^{nd}$ Ed. Academic Press, San Diego.

In the inflammatory phase, bacteria and debris are phagocytosed and removed, and factors are released that cause the migration and division of cells involved in the proliferative phase.

The proliferative phase is characterized by angiogenesis, collagen deposition, granulation tissue formation, epithelialization, and wound contraction. In angiogenesis, new blood vessels grow from endothelial cells. In fibroplasia and granulation tissue formation, fibroblasts grow and form a new provisional extracellular matrix (ECM) by secreting collagen and fibronectin. In epithelialization, epithelial cells migrate across the wound bed to cover the wound. In contraction, the wound is made smaller by the action of myofibroblasts, which establish a grip on the wound edges and contract themselves using a mechanism similar to that in smooth muscle cells. Unneeded cells undergo apoptosis when the cells' roles are close to complete.

In the maturation phase, collagen is remodeled and realigned along tension lines. Cells that are no longer needed are removed by apoptosis.

Wounds that fail to undergo closure in a normal course of time are termed chronic or non-healing wounds. See Lorenz et al. (2003) *Wounds: Biology, Pathology, and Management*. Stanford University Medical Center. Lower extremity skin ulcers can result from arterial or venous insufficiency. Factors that affect the repair process in non-healing ulcers are diabetic conditions, ischemia, bacterial infection, and nutrition. For diabetic conditions, the classical risk factors for developing ulcers are peripheral neuropathy, peripheral arterial disease, and susceptibility to infection. See Thuesen A. The University of Montana SPAHS Drug Information Service (2001) 5:1-3.

Treatment of Wounds

The primary goal in the treatment of diabetic foot ulcers is to obtain wound closure. Management of a foot ulcer is largely determined by its severity (grade), vascularity, and the presence of infection. A multidisciplinary approach should be employed because of the multifaceted nature of foot ulcers and the numerous comorbidities that can occur in patients with this type of wound. This approach has demonstrated significant improvements in outcomes, including reduction in the incidence of major amputation.

A mainstay of ulcer therapy is debridement of all necrotic, callus, and fibrous tissue. Unhealthy tissue must be sharply debrided back to bleeding tissue to allow full visualization of the extent of the ulcer and to detect underlying abscesses or sinuses.

Topical applications have been applied for the treatment of diabetic ulcers with some success. Examples include the use of placental extract, which contains various growth factors, and phenyloin for treating non-healing ulcers. See Chauhan et al. *Lower Extremity Wounds* (2003) 2:40-45. Another topical application, containing recombinant human platelet derived growth factor (PDGF), is Plermin, marketed by Dr. Reddy's Laboratories. Regranex® Becaplermin is the only FDA-approved topical platelet-derived growth factor (PDGF) for chronic diabetic neuropathic ulcers in USA. However, randomized controlled clinical trials showed only a 15% acceleration in the healing of neuropathic diabetic foot ulcers. See Falanga V. *Advanced Treatments Chronic Wounds* (April 2005)<http://www.worldwidewounds.com/2005/april/Falanga/Advanced-Treatments-Chronic-Wounds.html> February 2006. Although numerous topical medications and gels are promoted for ulcer care, relatively few have proved to be more efficacious than saline wet-to-dry dressings. Topical antiseptics, such as povidone-iodine, are usually considered to be toxic to healing wounds. Topical enzymes have not been proved effective for this purpose and should only be considered as adjuncts to sharp debridement. Soaking ulcers is controversial and should be avoided because the neuropathic patient can easily be scalded by hot water.

Growth factors besides PDGF have not been approved for clinical use and the results of clinical trials have not delivered the expectations generated by preclinical data. See Falanga supra. A possible explanation for this could be that growth factors are required in combination, or a different mode of delivery is required.

Cells are considered "smart materials" and can produce balanced mixtures of different growth factors and cytokines, as well as adapt their responses according to the environment they are in. Cells can themselves help in repairing affected area and damaged tissue. See Falanga, supra. Hence, cell-based applications have the more potential for much better results than the previously mentioned techniques.

With the advent of tissue engineering, there have been promising results shown by different skin substitutes in efficiently treating chronic wounds, which have otherwise been difficult to heal successfully and often lead to amputation of the limb having the ulcer. See Eisenbud et al. *Wounds* (2004) 16:2-17; Marston et al. *Diabetes Care* (2003) 26:1701-1705. While skin autografts are successful in effecting wound healing, the autografting procedure is invasive, painful and could lead to a secondary non-healing wound. In the case of chronic wounds, a skin substitute that can act as a temporary biological dressing and trigger tissue regeneration and wound healing by stimulating cells in the patient's own wound bed has the potential to be an effective treatment modality. Cells in the skin substitute may be effective delivery systems for growth factors that would help in stimulating the healing process. Cells that may be used in the skin substitute include dermal fibroblasts and keratinocytes from healthy skin biopsies.

Various skin substitutes have been developed internationally for the treatment of non-healing ulcers. Examples are Apligraf® (Organogenesis Inc.), Dermagraft® (Smith & Nephew Inc.), Oasis® (Healthpoint), and EZ Derm™ (Brennen Medical Inc.). These skin substitutes have shown good clinical results. However the skin substitutes face challenges such as difficult logistics of ordering and using the substitutes due to a cryopreservation requirement, difficulty in maintaining cell viability, poor durability of matrix collagen when exposed to the enzyme-rich wound bed (thereby causing cells to wash away and lose effect), and the thickness of the matrix preventing sufficient diffusion of growth factors from the embedded cells. Another pertinent problem is the cost of these skin substitutes. These challenges have lead to the requirement for improved and innovative solutions. The inventors of the present invention have been successful in providing an improved and alternate solution to the present skin substitutes by providing a temporary biological dressing or wound cover that causes wound healing by stimulating the patient's own tissue to regenerate.

In the emerging field of tissue engineering, there is a requirement for developing tissue equivalents for both in vivo and in vitro uses. In some tissue equivalents that have been developed, there is significant contraction their original size, which limits such equivalents to specific applications in which the contracted construct can be useful. See Clark et al. *J. Clin. Invest.* (1989) 84:1036-1040; Montesano et al. *Proc. Natl. Acad. Sci.* (1988) 85:4894-4897. Contracted tissue shrinks inwards immediate after release from a culture surface, while contractile macromass tissue constructs contract to a relatively smaller degree.

The tissue-like organization and constructs previously developed by the present inventors using the novel method of macromass culture (Indian Patent No. 195953 and U.S. patent application Ser. No. 10/686,822, filed Oct. 16, 2003) is an example of a tissue equivalent belonging to this contracting class. The constructs spontaneously reduce in size over a period of time. Another example is a multilayered sheet of keratinocytes, which contracts when detached without support from the culture vessel. See Green et al. *Proc. Natl. Acad. Sci.* (1979) 76:5665-5668.

Cellular sheets have been cultivated over different supporting layers, such as non-porous sheets. See Khor et al. *J. Mater. Sci. Mater. Med.* (2003) 14(2):113-20; Imaizumi et al. *Tissue Eng.* (2004) 10(5-6):657-64. However, non-porous supports limit the supply and diffusion of nutrients and gases. On the other hand, one problem of culturing cells using porous matrices is that a percentage of total cells seeded onto the sponge in the form of cell suspension leak out from the bottom of the sponge onto the base of the culture vessel. This problem has been recognized in earlier work in the field of cell culture methods. See Yang et al. *J. Biomed. Mater. Res.* (2002) 62(3): 438-446. This amounts to loss of cells when seeding, which is an especially critical problem for tissue engineering applications wherein cell sources can be rather limited. Loss of cells would also result in difficulty in getting reproducible constructs from equally seeded sponges, since variable numbers of cells would remain on the sponges if varying numbers of cells are lost while seeding. Methods such as anhydrous ammonia plasma treatment and ethanol treatment have been used for preventing cell loss.

In U.S. Pat. No. 5,273,900, an epidermal cellular sheet was made on one side of a porous collagen dermal substrate, which was prepared by making a non-porous collagen-laminating layer on one side of the porous dermal component to be able to form the epidermal sheet. The laminating layer does not and is not intended to enter into the porous dermal component, and it remains an integral part of the final product.

In another earlier invention involving methods for long-term culture of hematopoietic progenitor cells, the pores of a matrix are filled with a "gelatinous" substance. See Pykett et al., U.S. Pat. Nos. 6,645,489 and 7,192,769. However the gelatinous substance of this invention holds the cells within the pores of the matrix, and there is no sheet formation of the cells on one side of the matrix.

The present invention relates to an advances over the prior art that, for example, allow a tissue substitute to remain viable during transportation without any specific need for cryopreservation. In one embodiment, the present invention presents compositions and methods that addresses the needs of transporting a viable tissue substitute to a recipient's location.

SUMMARY OF THE INVENTION

The present invention provides a three-dimensional non-contractile tissue equivalent comprising a high density macromass cellular sheet comprising dermal fibroblast cells and a porous scaffold or matrix support, wherein the macromass cellular sheet is adhered to the surface the porous scaffold or matrix, and wherein the macromass cellular sheet does not contract from its original size.

In one embodiment of the present invention, the tissue equivalent the macromass cellular sheet is adhered to only one side of the porous scaffold or matrix.

In another embodiment, the dermal fibroblast cells comprise neonatal human dermal fibroblast cells.

In another embodiment, the porous scaffold or matrix is a sponge or a foam structure. The porous scaffold or matrix can comprise material chosen from chitosan, collagen, polyglycolic acid, and polylactic acid.

In another embodiment, the porous scaffold or matrix is a porous chitosan sponge. The porous chitosan sponge can be a flexible chitosan biopolymer sponge disk having a diameter of about 3.0 cm.

In another embodiment, the porous scaffold or matrix comprises pores that do not contact the macromass cellular sheet, wherein the pores are devoid of cells or liquid or solid matter therein.

In another embodiment, the porous scaffold or matrix is capable of holding moisture and allowing gas exchange.

In another embodiment, the macromass cellular sheet has a cell density of $1\times10^6$ cells per $cm^2$ to $12\times10^6$ cells per $cm^2$ of the porous scaffold or matrix.

In another embodiment, the cells in the macromass cellular sheet express vascular endothelial growth factor (VEGF) in an amount capable of inducing angiogenesis in a wound. The cells in the macromass cellular sheet are capable of expressing at least 40 ng of VEGF in 24 hours.

In another embodiment, the cells in the macromass cellular sheet express interleukin-8 (IL-8) in an amount capable of recruiting neutrophils to a wound. The cells in the macromass cellular sheet are capable of expressing at least 450 ng IL-8 in 24 hours.

In another embodiment, the cells in the macromass cellular sheet express at least one gene encoding a protein chosen from transforming growth factor α (TGF-α), transforming growth factor β1 (TGF-β1), basic fibroblast growth factor (bFGF), platelet derived growth factor (PDGF), keratinocyte growth factor (KGF), collagen type I, collagen type III, fibronectin and syndecan 2.

In another embodiment, the thickness of the porous scaffold or matrix does not impede diffusion of growth factors. The porous scaffold or matrix can have a thickness of about 1.5 mm.

In another embodiment, at least 98% of the cells do not express HLA-DR surface protein.

In another embodiment, the tissue equivalent is packaged in a sterile pouch comprising sterile transport medium.

In another embodiment, the dermal fibroblast cells are at least 90% viable for up to 72 hours at 2-8° C.

In another aspect of the present invention, a methodology is provided for treating a wound on skin comprising applying to the wound a three-dimensional non-contractile tissue equivalent comprising a high density macromass cellular sheet comprising dermal fibroblast cells and a porous scaffold or matrix support, wherein the macromass cellular sheet is adhered to the surface the porous scaffold or matrix, and wherein the macromass cellular sheet does not contract from its original size.

In one embodiment, the method further comprises directly contacting the macromass cellular sheet with the wound and transferring cells from the macromass cellular sheet to the wound. The wound can be an ulcer selected from a diabetic ulcer, pressure ulcer or a venous ulcer. The ulcer can be located on a foot.

In a further aspect of the present invention, a methodology is provided for testing the safety of an anti-cancer compound comprising contacting the compound with a three-dimensional non-contractile tissue equivalent comprising a high density macromass cellular sheet comprising dermal fibroblast cells and a porous scaffold or matrix support, wherein the macromass cellular sheet is adhered to the surface the porous scaffold or matrix, and wherein the macromass cellular sheet does not contract from its original size, and examining viability of the cells within the macromass cellular sheet. In one embodiment, at least 99% of the cells within the macromass cellular sheet are normal quiescent human cells.

In a further aspect of the present invention, a process is provided for preparing a three dimensional non-contractile tissue equivalent comprising a macromass cellular sheet of dermal fibroblast cells adhered to a porous scaffold or matrix, wherein the method comprises absorbing a liquid blocking agent into pores of the porous scaffold or matrix, solidifying the blocking agent, culturing dermal fibroblast cells onto the surface of the porous scaffold or matrix to form a multilayered high density macromass cellular sheet, and desolidifying and removing the blocking agent.

In one embodiment, the culturing step comprises macromass culturing of dermal fibroblast cells onto only one side of the porous scaffold or matrix. The dermal fibroblast cells can comprise neonatal human dermal fibroblast cells.

In another embodiment, the blocking agent comprises material chosen from gelatin, alginate, pectin, agar and agarose.

In another embodiment, the porous scaffold or matrix comprises material chosen from chitosan, collagen, polyglycolic acid, and polylactic acid.

In another embodiment, the dermal fibroblast cells are not lost by leaking through the pores of the porous scaffold or matrix during the culturing step.

In another embodiment, at least $20\times10^6$ dermal fibroblast cells are seeded onto the porous scaffold or matrix during the culturing step. The macromass cellular sheet can have a cell density of $1\times10^6$ cells per $cm^2$ to $12\times10^6$ cells per $cm^2$ of the porous scaffold or matrix.

In another embodiment, the cells in the macromass cellular sheet express VEGF and/or IL-8 in an amount greater than would be expressed by the same cells in a monolayer having the same diameter as the macromass cellular sheet.

BRIEF DESCRIPTION OF THE DRAWINGS

The following drawings form part of the present invention and are included to substantiate and demonstrate the important aspects of the disclosure. The present invention may be better understood by the following drawings in combination with the detailed description of embodiments presented herein.

FIG. 1: (A) The top view of the three dimensional tissue equivalent mounted on one side of a porous chitosan sponge disc, which is aseptically packed in a sterile square biocompatible pouch containing sterile transport medium. The pouch is contained in an outer square plastic cassette. (B) The tissue equivalent after incubation in thiazolyl blue tetrazolium bromide (MTT) solution with the cellular sheet turned dark on the white sponge.

FIG. 2: Depicts cell loss through a chitosan sponge when seeding. This is a representative microscopic view of the base of the culture dish in which a chitosan sponge was placed for seeding, after the sponge was removed from the dish. Here, the chitosan sponge used during seeding was not filled with gelatin solution, hence pores in the sponge were not blocked, and a large number of cells leaked out. By contrast, in the present invention, no cells were lost from a sponge that was filled with gelatin (not shown).

DESCRIPTION OF THE INVENTION

Figure 3:
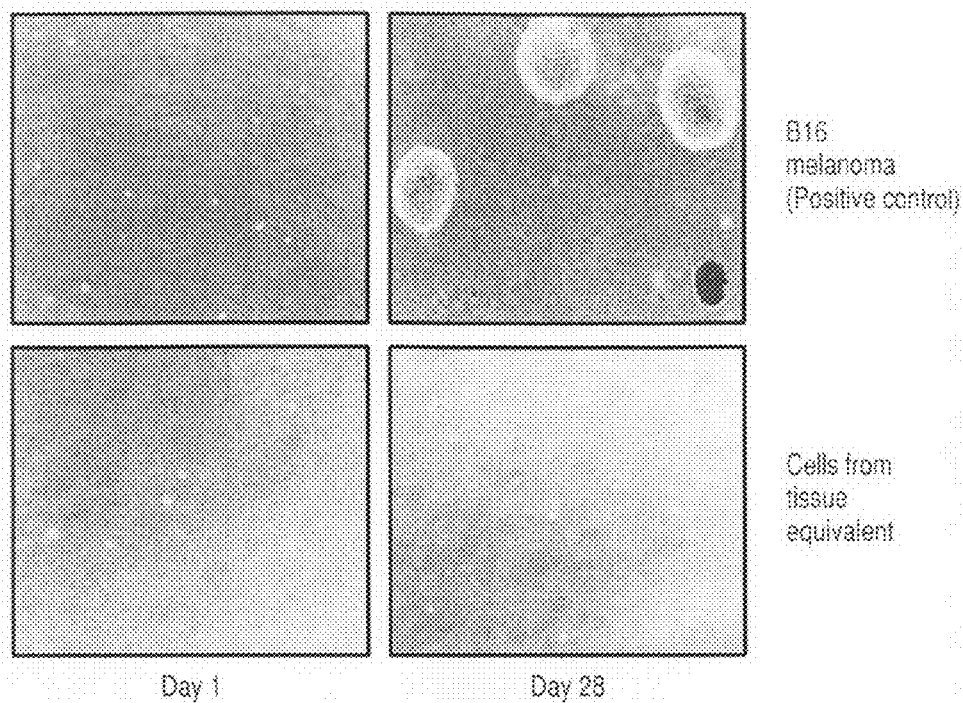
FIG. 3: Illustrates the in vitro tumorigenicity results of soft agar assay of cells isolated from the tissue equivalent of the present invention, wherein cell line B16 melanoma was a positive control.

In order to provide effective treatment for non-healing ulcers, the inventors of the present invention have developed a temporary dermal wound dressing intended for use in the treatment of non-healing ulcers, not limited to diabetic ulcers of the skin. It comprises a three-dimensional multilayered tissue-like sheet of cells, such as neonatal human dermal fibroblasts, mounted on one side of a porous scaffold or matrix support, such as a chitosan sponge.

The present invention provides a non-contractile three dimensional tissue equivalent with high cell density comprising a multilayered cellular sheet of cells mounted onto a porous scaffold or matrix. In one embodiment of the invention, the cells are dermal fibroblasts. In another embodiment, the present invention provides a non-contractile three-dimensional tissue equivalent comprising a macromass cellular sheet adhered on one side of a porous scaffold. In a further embodiment, the present invention provides a three-dimensional tissue equivalent that comprises neonatal human dermal fibroblasts in a three-dimensional sheet configuration, mounted onto one side of a porous chitosan biopolymer sponge disc. The three-dimensional tissue equivalent may be a circular flexible disc of diameter 3.0 cm and contains about $25 \times 10^6$ viable neonatal human dermal fibroblasts. In a further embodiment, the three-dimensional tissue equivalent is used for wound dressing. In a further embodiment, the present invention is directed toward the treatment of non-healing ulcers, such as diabetic ulcers of the skin.

The present invention also provides methodology for the preparation and use of a three dimensional non-contractile tissue equivalent comprising a macromass cellular sheet of cells, such as dermal fibroblast cells, adhered to a porous scaffold or matrix. Methods of the present invention involve culturing cellular sheets of cells over porous scaffolds or matrices. In one embodiment, the method comprises absorbing a liquid blocking agent into pores of a porous scaffold or matrix, solidifying the blocking agent, culturing dermal fibroblast cells onto the surface of the porous scaffold or matrix to form a multilayered high density macromass cellular sheet, and desolidifying and removing the blocking agent. Here, the blocking agent, such a gelatin-blocking component, does not form a laminating layer on one side, but enters and fills the pores of a porous scaffold or matrix support, such as a chitosan sponge, and does not remain a part of the final non-contracting tissue equivalent.

In one embodiment, the present invention provides a three dimensional tissue equivalent that provides cells in a high cell density configuration and having direct contact of the cellular sheet with the wound bed, therefore aiding in accelerated wound healing. In another embodiment, the preparation of the tissue equivalent, including culturing cells on one side of the three-dimensional tissue equivalent, produces minimal cell loss. In a further embodiment, the cultured cells are maintained for a suitable period of time. In a further embodiment, the present invention provides a three dimensional tissue equivalent that allows the cells to migrate to a suitable substratum (such as a wound bed), and to further proliferating on the substratum.

In one aspect of the present invention, methodology is provided for using the tissue equivalent, including an in vitro method for testing the safety of anti-cancer compounds and methods for treating wounds on the skin, such as foot ulcers.

In another aspect of the present invention, tissue equivalents are provided that allow for easy diffusion of growth factors from cells in the tissue equivalent into a wound by directly contacting the cellular sheet with the wound bed. In one embodiment, the thickness of the tissue equivalent does not impede diffusion of growth factors.

In a further aspect of the present invention, a three-dimensional tissue equivalent expresses or produces enhanced amount of cell-regulating factors. In one embodiment, the present invention provides a three-dimensional tissue equivalent that expresses or produces an enhanced amount of VEGF, therefore causing local angiogenesis in a wound bed. The high levels of IL-8 are expected to improve clearance of bacteria by recruiting neutrophils to the wound site. Local therapeutic angiogenesis, by delivery of angiogenic growth factors, is considered to be a promising approach in the treatment of ulcers associated with ischemia or peripheral arterial disease. See Di Stefano et al. *Ital. Heart. J.* (2004) 5:1-13.

Another factor believed to contribute to the non-healing condition is chronic bacterial colonization. Interleukin-8 also has been shown to improve wound healing efficacy. See Feugate et al. *J. Cell Biol.* (2002) 156:161-172. In another embodiment, the present invention provides a three dimensional tissue equivalent that further produces enhanced amount of Interleukin-8 (IL-8), which aids in improving the clearance of bacteria by recruiting neutrophils to the wound site, therefore resulting in wound healing efficacy.

In a further embodiment, the present invention provides a three dimensional tissue equivalent with enhanced VEGF and IL-8. The high levels of VEGF are expected to induce angiogenesis in the wound bed. In a further embodiment, a single three-dimensional tissue equivalent of the present invention secretes about 40 ng of VEGF and about 450-1000 ng of IL-8 in 24 hours after opening the package, under in vitro conditions. The tissue-like sheet also expresses other growth factors and extracellular matrix proteins involved in wound healing, such as transforming growth factor β1 (TGFβ1), keratinocyte growth factor (KGF), basic fibroblast growth factor (bFGF), transforming growth factor α (TGFα), platelet derived growth factor (PDGF), collagen type I, and collagen type III. See Rosenberg et al. (2005) "Wound healing, Growth factors." EMedicine.com <http://www.emedicine.com/plastic/topic457.htm> June, 2006.

In another aspect of the present invention, a three dimensional tissue equivalent with a based matrix is highly porous and allows efficient gaseous exchange to prevent the buildup of toxic or unhealthy gases within the wound and to promote natural healing. In one embodiment, the present invention does not allow the accumulation of exudates produced by the wound, enabling the exudates to ooze out from the edges of the porous sponge disc, where the tissue sheet is not present (e.g., about 2-3 mm along the edge of the circular sponge base). In another embodiment, the matrix is chitosan, a natural biocompatible polymer sponge. In a further embodiment, the based matrix is also hydrophilic and its porous nature helps maintain a moist wound environment, which is important in promoting wound healing. See Bryan J. *J. Wound Care* (2004) 13:227-228.

In a further aspect of the present invention, a three-dimensional tissue equivalent is very flexible and is expected to fall in shape with the contours of the wound, improving contact with secreted growth factors. In one embodiment, the wound is a diabetic foot ulcer. The tissue equivalent of the present invention is not fragile, and is easy to handle with forceps, and provides visualization of the tissue sheet.

In a further aspect of the present invention, the three-dimensional tissue equivalent is individually and aseptically packaged in a specially designed sterile square pouch for transportation, which contains 2.5 ml of sterile transport medium. The pouch is contained in an outer square plastic cassette in which a large portion of cells within the tissue equivalent remain viable during transportation without any specific need for cryopreservation and can be transported to the recipient's location.

The features of the three-dimensional tissue equivalent of the present invention may include the following:
1. It provides cells in a three-dimensional configuration, supported by a matrix that is porous.
2. It provides cells at a high cell density.
3. It provides cells with high percentage of viability.
4. It can express or produce enhanced amount of VEGF and IL-8, and allows easy diffusion of growth factors to the wound bed, which aids in healing of ulcers.
5. It enables direct contact of the cells with the wound bed, with no matrix between the cell sheet and the wound bed, because the cell sheet may be formed entirely on one side of the matrix.
6. It enables transfer of cells to the substratum, such as the wound bed.
7. It is flexible, enabling it to adhere to any site of the wound, especially on the foot.
8. It has a porous scaffold, so it can hold moisture and therefore providing a conducive environment for faster healing.
9. It has a porous scaffold, thereby allowing gas exchange, which aids in preventing the build-up of gases in the wound bed.
10. It does not allow any accumulation of exudates from the wound.
11. It does not require cryopreservation, thus reducing the transport costs.
12. It provides cells that are viable up to 72 hours at 2-8° C.
13. It provides a cost effective tissue substitute.
14. It is safe and is efficient in treating wound ulcers.

DEFINITIONS

The term "three dimensional tissue equivalent" as used herein refers to a three-dimensional arrangement of dermal fibroblast cells to form a tissue-like cellular sheet construct and a three-dimensional structure of matrix.

The term "cell loss" as used herein refers to cells not incorporated into the tissue-like sheet and are lost during the seeding of the cells to form a tissue-like cellular sheet.

The term "non contractile" as used herein refers to a tissue equivalent, wherein the edges of the tissue-like sheet do not contract when placed on a substrate and retains its initial size and shape in the stretched form.

The term "high density" as used herein refers to a high seeding density of cells within a range favorable for the formation of tissue-like organization. In one embodiment, high cell seeding density is in a range of $1\times10^6$ to $10\times10^6$ per $cm^2$, where cells are settled together within the three-dimensional space that is occupied by the cells at the base of the culture vessel. At a high cell density, cells come into a state of close proximity with one another that triggers or signals them into a tissue formation mode by which they become cohesively integrated.

The term "macromass cellular sheet" as used herein refers to a cellular sheet wherein the sheet formed is visible to the naked eye and is made by the macromass culture method, discussed ahead.

The term "porous scaffold or matrix" as used herein refers to a scaffold or matrix that has open pores that can be filled with another substance.

The term "blocking agent" as used herein refers to a substance that can fill in the pores of a porous scaffold or matrix, solidify, and therefore block the pores. One example is gelatin.

The term "macromass culture" or "macromass culturing" as used herein refers to the formation of macroscopic three-dimensional tissue-like constructs in culture, wherein "macroscopic" means that the size of the tissue is at least such that it can be visually discerned by the normal unaided human eye. "Macromass culture" may also refer to a culture system for three-dimensional tissue-like formation or organization of cells, in which cells are seeded at a high density per unit area or space of a culture vessel and there is no requirement for any other agents that aid in tissue formation. "Macromass culture" may also refer to a method of generating a three-dimensional tissue-like organization, macroscopic or microscopic, from cells by high-density cell seeding. This method brings cells together in close proximity in a certain favorable range of high densities of cells in three-dimensional space, which favors cohesive integration of cells into a three-dimensional tissue-like state, there being no requirement for any other agents that aid in tissue formation. Examples of "macromass culturing" techniques are described in U.S. patent application Ser. No. 10/686,822, India application Ser. No. 912/MUM/2002, and International Application Ser. No. PCT/IN2004/000086, all of which are hereby incorporated by reference. See also, Deshpande M, *Biotechnol Appl Biochem.* (2007), July 11, PMID: 17623015, DOI:10.1042/BA20070120, describing that, by macromass culture, dermal fibroblasts can be made to organize themselves into a unified three-dimensional form without the aid of a scaffold, and macroscopic constructs, named macromasses, can be made wholly from cells. The sole factor causing three-dimensional organization is culture of cells at high cell seeding density per unit area. See Deshpande, supra. No scaffold or extraneous matrix is used for generation of macromasses, they are of completely cellular origin. See Deshpande, supra. No other agents or external influences such as tissue-inducing chemicals, tissue-inducing growth factors, substratum with special properties, rotational culture, centrifugation, etc, are employed for macromass formation, and all seeded cells become part of the cohesive construct. See Deshpande, supra. These three-dimensional constructs have the potential for use as in vitro tissue analogues, and a possible application for in vitro cytotoxicity testing is demonstrated. See Deshpande, supra.

The present invention describes the development of a non-contractile tissue-equivalent, which is a dermal wound dressing, based on the tissue-like constructs made by macromass culture. The present invention has developed a novel method under the present invention, which helps in obtaining non-contractile macromass tissue-like constructs.

In one embodiment, the present invention is the delivery of the non-contractile tissue like construct, wherein the tissue construct becomes adhered to a support while ensuring that few cells are lost during formation. The present invention encompasses a method for delivering the macromass cellular sheet tissue-like construct in a non-contractile form that it is held to a support in its original size. In order to achieve the adherence of the tissue like construct to a support, a support with a rough surface or support may be used, as well as one that is porous to allow the exchange of nutrient and gas. Thus, in one embodiment, the present invention uses a porous support with a rough surface, as this has proved to be more effective in producing the desired result of the invention because the tissue sheet does not adhere well to a smooth surface. Thus, the present invention encompasses the use of a porous sponge or matrix whose surface is not smooth due to the microscopic projections.

In selecting a porous rough surface for support, however, a challenge existed to prevent cell loss from the porous support when preparing the tissue equivalent, namely during the seeding step. However, one methodology in the present invention, as detailed herein the specification, involves effectively culturing the macromass cellular sheet over the surface of a porous rough support, such as a chitosan sponge, under conditions that prevents leaking of cells from the tissue equivalent. In one embodiment, the tissue-like cellular sheet is formed entirely on one side of the sponge and adheres well without coming off, even with prolonged incubation, thus rendering it non-contractile without reduction in its original size throughout.

The present invention further describes a method for seeding of porous three-dimensional matrices or biodegradable or non-degradable porous polymer scaffolding matrix having a sponge or foam structure without cell loss through the pores of porous matrices when seeding the porous matrix with cells.

According to the method of the present invention, the porous matrix having a sponge or foam structure, prior to seeding of cells, is placed in a culture dish containing a molten solution of a substance, e.g., gelatin, such that the molten solution is absorbed into the pores of the sponge. Suitable conditions are maintained so that the molten solution solidifies or sets, within the pores of the sponge. The cells are then seeded onto the porous matrix having a sponge or foam structure and allowed to attach to the upper surface of the sponge or foam, under conditions in which the solution of blocking substance remains solidified. Tissue-like organization of cells by macromass culturing method takes place during this time, enough to result in cohesion of cells such that the cells are not free any longer, but attached to each other and the top surface of the sponge. After allowing formation of the macromass cellular sheet, the conditions of incubation of the assembly are changed to one that causes the solution of gelatin to liquefy and drain out of the pores of the sponge or foam, into the culture medium in subsequent washings. The cells are already integrated into the macromass sheet, so they do not disperse through the pores even after the gelatin has liquefied.

Thus, in the present invention, the pores of a porous matrix are temporarily filled or blocked with a substance for the purpose of preventing cell loss by not allowing cells to leak through while seeding. The blocking substance is later removed from the porous matrix, after cells have formed the macromass cellular sheet on one side of the sponge, to regain porosity or "openness" of pores of the sponge. In the present invention, cells are not intended to be entrapped within or impregnated into the substance that is used for blocking. The role of the blocking substance in the present invention is to block or prevent the entry and passage of cells into the porous matrix. The blocking substance is temporary in nature, and does not remain to be an integral part of the final tissue equivalent.

The porous matrix used in the method of the present invention may be of varying pore size. The porous matrix used in the method of the present invention is formed of material selected from the group not limited to gelatin, chitosan, collagen, polyglycolic acid, polylactic acid, alginate. In one embodiment, chitosan is used selected as a porous matrix. Chitosan is a natural biocompatible polymer, which is obtained by the alkaline deacetylation of chitin, which is derived from the exoskeletons of crustaceans such as crabs. Shi et al. *J. Surg. Res*. (2006) 133:185-192. Chitin is a co-polymer of N-acetyl-glucosamine and N-glucosamine linked by glycosidic bonds.

The blocking/filing agent used in the method of the present invention may be selected from the group not limited to gelatin, alginate, pectin, agar, agarose.

In the Pykett invention discussed supra, the rationale for using a gelatinous substance is to impregnate the cells into it to provide attachment and a three-dimensional environment within the pores of the matrix. In the present invention, by contrast, the rationale of using gelatin is to keep cells out of the porous matrix during seeding, to allow them to form a macromass cellular sheet, for example, entirely on one side of the matrix. Secondly, in the Pykett invention, the gelatinous substance after achieving solidified state, remains in the final product, becoming an integral part of it—there is no reliquidification of the gelatinous substance. In the present invention, the gelatin is removed after cell sheet formation, by changing conditions to liquefy it. Thirdly, in the Pykett invention, the list of exemplary "gelatinous" substances actually does not include gelatin itself. This is because feasible concentrations of gelatin cannot be maintained in a solid state at 37° C., which is the optimal incubation temperature for cells, and the gelatinous substance is required to be solid at 37° C. in that invention. However, in the present invention, gelatin is used because it is a substance that would liquefy at 37° C.

The present invention thus provides a three-dimensional tissue equivalent that can be used as dermal dressing for various wounds not limited to diabetic ulcers, pressure ulcers and venous ulcers.

Additionally, the tissue-equivalent of the present invention has been shown to have potential as an in vitro model of normal non-dividing cells for safety testing. Many anti-cancer drugs are developed based on the principle that they act on rapidly dividing cells (cancerous cells) and not on quiescent cells (normal cells of the body). This is important because the anti-cancer drug should not kill normal cells while destroying cancerous cells. Hence, in the development of anti-cancer drugs that act by destroying rapidly dividing cells, it is important to establish its safety towards normal cells. An in vitro model to establish this safety would be useful, especially because safety testing in animals is minimized by the use of in vitro alternatives.

The following examples are included to demonstrate different embodiments of the invention. It should be appreciated by one skilled in the art that the techniques disclosed in the examples which follow represent techniques discovered by the inventor to function well in the practice of the invention, and can therefore be considered to constitute embodiments for its practice. However, one skilled in the art should, in light of the present disclosure, appreciate that the specific embodiments disclosed do not limit the invention and modifications to the embodiments can be made that would fall within the scope of the invention.

Example 1

Preparation of the Three Dimensional Tissue Equivalent

I. Cell Isolation and Culture.

In the present invention, human dermal fibroblasts were isolated from discarded human skin biopsies obtained with written informed consent. The dermis was separated from the epidermis by treatment with Dispase (Sigma, St. Louis, USA). The dermis was minced and digested with 0.01% collagenase in DMEM+10% FCS overnight and then cells were allowed to attach to a culture flask. Cells were cultured in DMEM+10% FCS at 37° C. in 5% $CO_2$ and subcultured using Trypsin-EDTA solution.

II. Preparation of Chitosan Sponges.

Chitosan sponges having a diameter of 3.0 cm and thickness of about 1.5 mm were prepared by lyophilization of frozen chitosan solution in 3.5 cm dishes. After lyophilization, the chitosan sponges were stabilized in isopropanol. The chitosan sponges were treated with ammonia and methanol solution. Chitosan sponges were rinsed with water for 3 hours with shaking. Chitosan sponges were then equilibrated in isopropanol. Chitosan sponges were then gamma-irradiated in pouches containing Vitamin E dissolved in isopropanol. Gamma-sterilized chitosan sponges were subsequently rinsed in isopropanol and soaked in serum-free medium overnight at 37° C.

III. Preparation of Three-Dimensional Non-Contractile Tissue Equivalent

A tissue equivalent comprising a chitosan sponge with macromass tissue-like organization of dermal fibroblasts on one side was prepared.

Gelatin weighing 1.0 g. was dissolved in 10 ml Dulbecco's phosphate buffered saline by heating in a microwave oven. The gelatin solution was filter-sterilized through 0.2 μm syringe filter while molten and poured into 3.5 cm dishes, about 3.0 ml per dish. Chitosan sponge, pre-soaked as above, was placed in the molten gelatin solution and pressed with forceps so that the gelatin entered and completely filled the pores. Each gelatin-soaked chitosan sponge was transferred to another 3.5 cm dish, which was then placed in a refrigerator to set the gelatin within the sponge. Dermal fibroblasts were harvested from culture flasks and collected in a tube in growth medium. The cells were counted in a cell counting chamber. For each tissue equivalent, a volume of cell suspension containing $25 \times 10^6$ total cells was transferred to a fresh tube. The cells were pelleted at 1000 rpm for 5 minutes and resuspended in 2.0 ml medium with 10% fetal bovine serum. The chitosan sponge was removed from the refrigerator and brought to room temperature for 5 minutes. The excess set gelatin from the top of the sponge was scraped away by gently scraping using a cell scraper. A sterile stainless steel ring of outer diameter 3.3 cm, inner diameter 2.5 cm, and thickness or height of 0.4 cm was placed over the sponge.

The 2.0 ml cell suspension containing $25 \times 10^6$ cells was seeded over the sponge, within the stainless steel ring. This gives a seeding density of $5 \times 10^6$ cells per $cm^2$, since the area within the ring is 5 $cm^2$. The dish was carefully placed in an incubator at 28-29° C. for 2 hours and 15 minutes. The gelatin was semi-solid at this temperature. The dish was then carefully transferred to a 37° C. $CO_2$ incubator and incubated for 2 hours and 15 minutes. The gelatin liquefies at this temperature. The dish was removed from the incubator and the stainless steel ring was removed by lifting. The tissue equivalent of the present invention was carefully lifted using forceps, holding at the edge and placed in a dish containing 25 ml growth medium. The tissue equivalent of the present invention was incubated at 37° C. in an $CO_2$ incubator overnight, which allowed full formation of the macromass cell sheet adhered to the chitosan sponge, and allowed the gelatin to leach out of the sponge into the medium, causing removal of gelatin. The tissue equivalent of the present invention was then transferred to a fresh dish containing fresh growth medium and subsequently packaged in transport medium in a pouch (FIG. 1A). To better visualize the macromass cellular sheet on the chitosan sponge, the tissue equivalent was incubated in MTT solution so that the cells, being viable, formed a dark purple colour. (FIG. 1B).

IV. Evaluation of Cell Loss Through Sponge.

The 3.5 cm dish in which seeding was done was assessed for cell loss by viewing the dish under the microscope for presence of cells attached to the base of the dish. It was found that substantial number of cells had been lost from control sponges that had been seeded with same number of cells, but had not been filled with gelatin solution. The results are depicted in FIG. 2. There was no or negligible cell loss from the sponge filled with gelatin before seeding. Thus, in this embodiment of the present invention, cell loss from a chitosan sponge was successfully prevented by using the method of this invention. As can be seen from the method used to prevent cell loss as described above, cell-friendly agents like gelatin and phosphate buffered saline were used.

Example 2

Characterization and Evaluation of Three Dimensional Tissue Equivalents

The three dimensional tissue equivalent of the present invention was evaluated for safety and effectiveness, and the data are classified below in four categories: (1) Safety, (2) Potency, (3) Purity, and (4) Stability.

1. Safety

A) Sterility

To ensure that aseptic conditions were maintained from the manufacturing process until final packing, the batches of tissue equivalent of the present invention were tested for sterility to detect the presence of aerobic and anaerobic microbes. This test was performed using the Direct Inoculation method (IP, 1996), which involved inoculating the test sample in two different sterile nutritive media, namely, Fluid Thioglycollate Medium (FTM) and Soybean Casein Digest Medium (SCDM). Absence of growth in the inoculated media during the incubation period of 14 days confirmed the sterility of the samples.

B) Bioburden

The microbial load in terms of number of colonies appearing on plates of solid medium was checked as index of the microbial density or bioburden entirely during the manufacturing process and the packed product. The final spent transport medium was also tested for microbial burden. Test results indication there was no bioburden.

C) In Vitro Tumorigenicity

The tumorigenicity of the tissue equivalent of the present invention was tested by soft agar assay. In this assay, tumorigenic cells, which are not dependent on attachment, form colonies, while normal cells which are dependent on attachment, do not form colonies. While a positive control cell line B16 melanoma formed colonies within 28 days of incubation, the cells from tissue equivalent of the present invention did not form colonies and remained as single cells, thus confirming that the cells are non-tumorigenic and the process does not induce tumorigenicity. A representative result is depicted in FIG. 3.

D) Karyology

Figure 4:
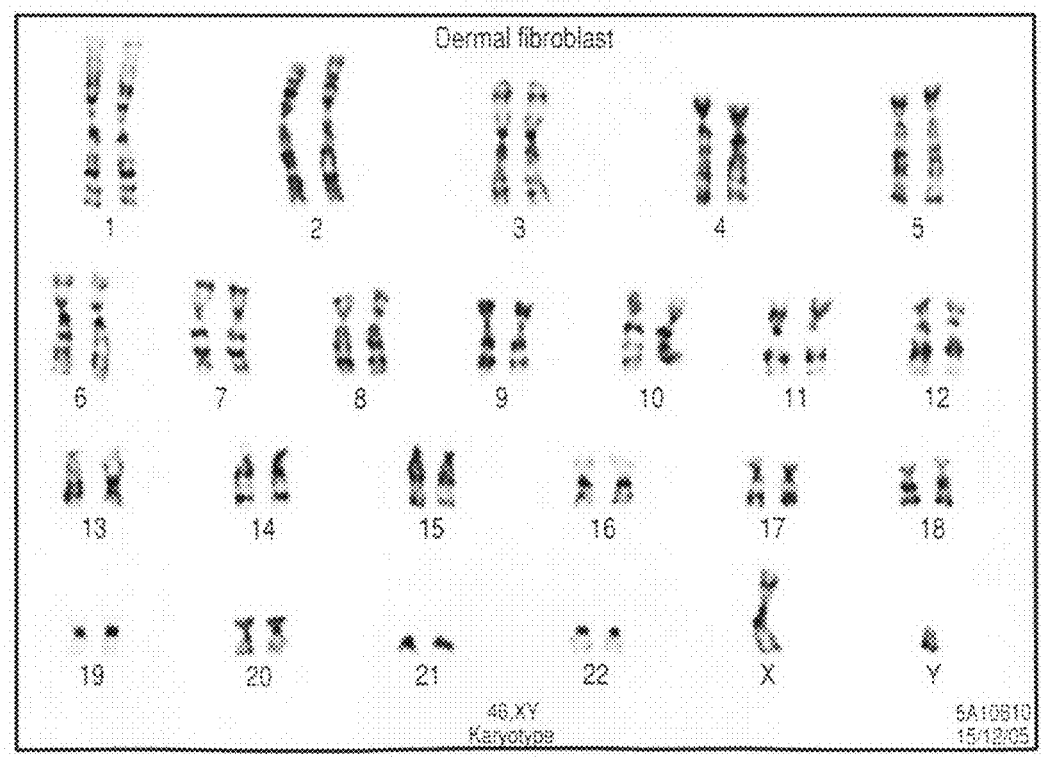
FIG. 4: Illustrates a representative normal karyogram of cells isolated from the tissue-equivalent of the present invention.

The chromosomal abnormalities of the tissue equivalent of the present invention was analyzed by karyotyping, wherein the dermal fibroblast were extracted from the tissue equivalent and plated and then karyotyped. The test confirmed that the cells have a normal karyotype with no detectable chromosomal abnormalities as shown in the FIG. 4.

E) Expression of HLA-DR Surface Protein

Figure 5:
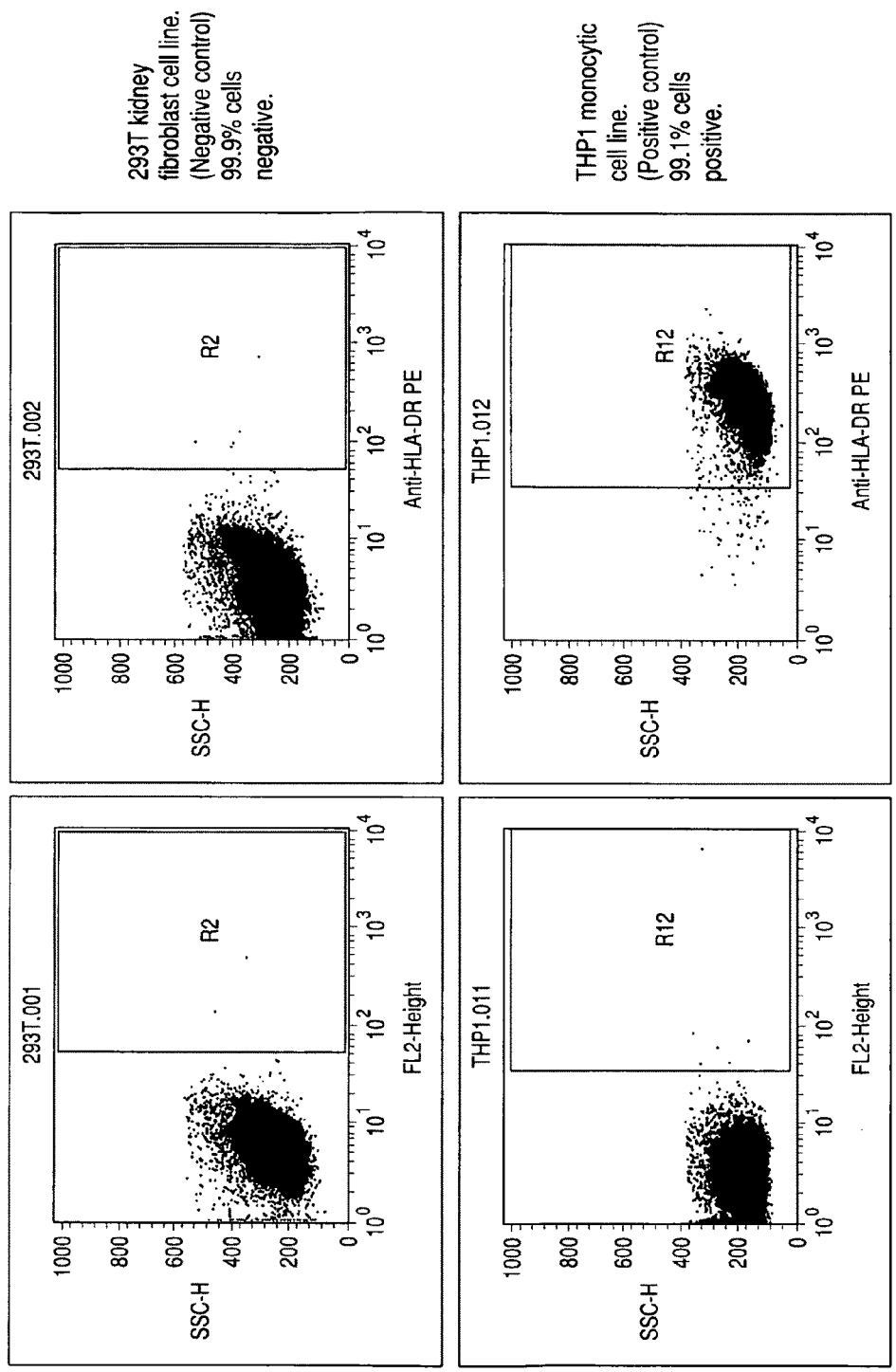
FIG. 5: Illustrates the analysis of extracted fibroblasts from the tissue equivalent of the present invention for expression of HLA-DR surface protein by fluorescence activated cell sorting (FACS).
Figure 5:
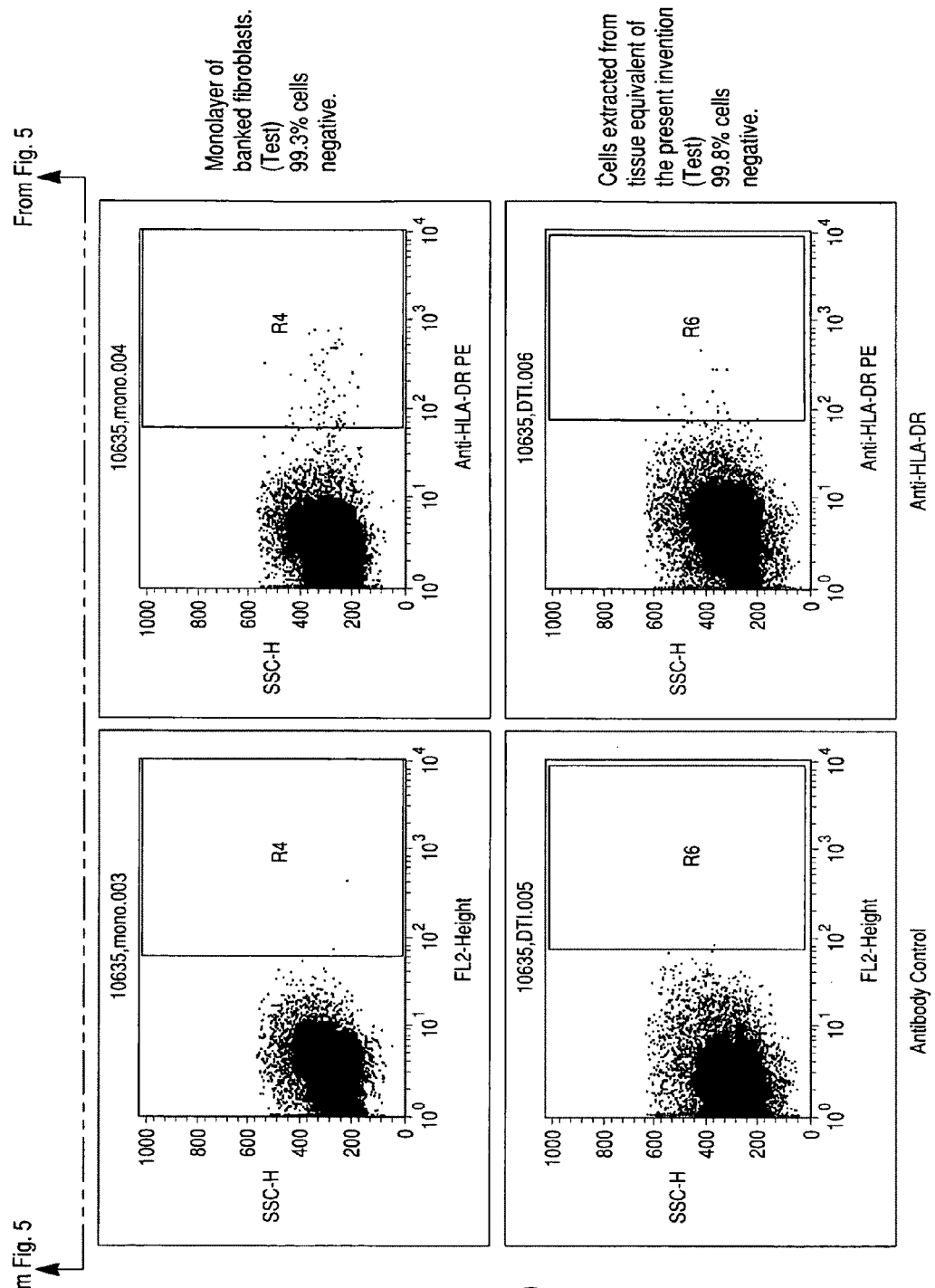

The human leukocyte antigen-DR (HLA-DR) is a class II major histocompatibility complex cell surface reporter encoded by the human leukocyte antigen complex on chromosome 6, region 6p21.31. HLA-DR is present on the surface of cells and is responsible for the immune rejection of allogeneic cells. See Bach F H. *Immunol. Lett*. (1989) 21(1):21-4. Banked cells (cells that were stored or cryopreserved until passage 7 or greater) were used for preparing the tissue equivalent of the present invention were, in order to be at least 98% negative for HLA-DR surface protein expression. In order to ensure that the process of preparing tissue equivalent of the present invention from these banked cells did not further enhance the surface expression of HLA-DR protein, the fibroblasts were extracted from the prepared tissue equivalent of the present invention and analyzed by fluorescence activated cell sorting (FACS). It was found that the extracted cells extracted did not have enhanced expression of HLA-DR surface protein compared to the banked cell monolayers. The extracted cells were also 98% negative for HLA-DR, indicating that 98% or more of the cells did not have the HLA-DR protein on their surface. A representative result is shown in FIG. 5.

2. Potency

A) Histology

Figure 6A:
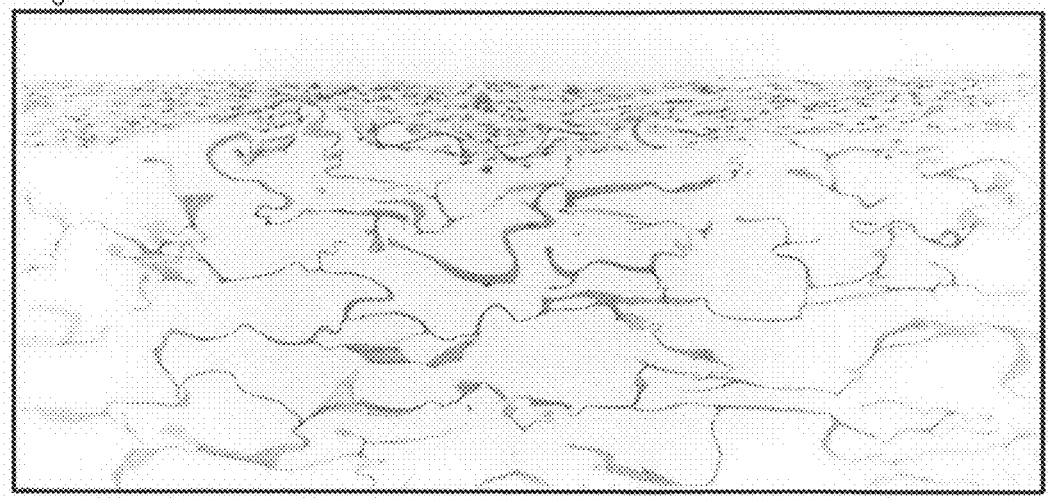
FIG. 6: Illustrates histology showing haematoxylin and eosin staining of a vertical section through the tissue equivalent of the present invention, demonstrating the multilayered organization of cells, at a high density, which would contribute to accelerated wound healing. It also shows the highly porous nature of the supporting matrix. The macromass cellular sheet is seen adhered to one side of the sponge, the pores of which are "open." (A) High power view. (B) Low power view.
Figure 6B:
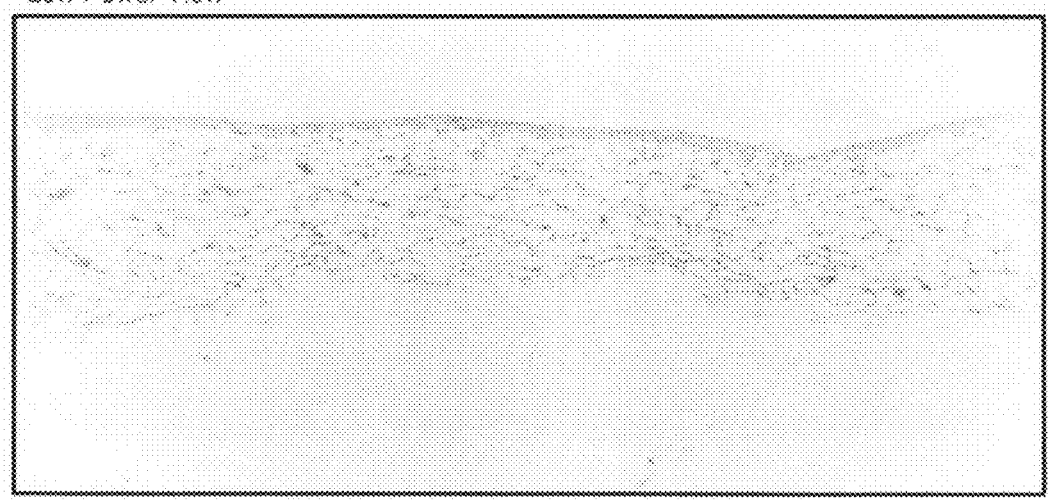

In one embodiment, the tissue equivalent of the present invention comprises a three-dimensional organization of cells. The three-dimensional organization of the fibroblasts will give better results in wound healing, as compared to a monolayer of cells. Therefore, to confirm the three-dimensional nature of the tissue equivalent of the present invention, histological examination was performed. FIG. 6 shows the hematoxylin and eosin staining of a vertical section through the tissue equivalent, demonstrating the multilayered organization of cells, which can also be seen to be at a high density. FIG. 6A shows the high-power view and FIG. 6B shows the low power view, wherein both top and lower sides of the chitosan sponge are encompassed in the picture.

It can be seen from FIG. 6 that the cellular sheet is entirely on one side of the sponge. FIG. 6 also shows the highly porous nature of the chitosan scaffold, which is also an important attribute in the mechanism of action of the tissue equivalent of the present invention, since the porous nature would allow gas exchange and help in maintaining a moist wound environment. Also, it can be seen from the figure that the cellular sheet on one side of the sponge would be in direct contact with the wound, allowing efficient diffusion of growth factors from the tissue equivalent to the wound bed, there being no matrix impeding the diffusion. It can also be seen from the figure that the pores of the sponge are "open," in that they are devoid of integrated matter filling or occupying them. This is in contrast to other porous scaffolds, wherein the pores become occupied with a filling material and/or cells and extracellular matrix synthesized by the cells such that the pores are no longer "open" in the final construct.

B) Viability of Cells

For the tissue equivalent of the present invention to be efficacious, it is important that the viability of the cells in the tissue equivalent after preparation is high. The cells were extracted from the tissue equivalent by trypsinization and suspended. The viability of the extracted single cell suspension was determined using the vital dye Trypan Blue, and counted using a counting chamber. It was found that cells in the prepared tissue equivalent had a viability of at least 90%, which contributes to the high efficacy of the product. This high viability also indicates that the process used to prepare the tissue-equivalent without cell loss is cell-friendly.

C) Expression of Genes Involved in Wound Healing

Figure 7:
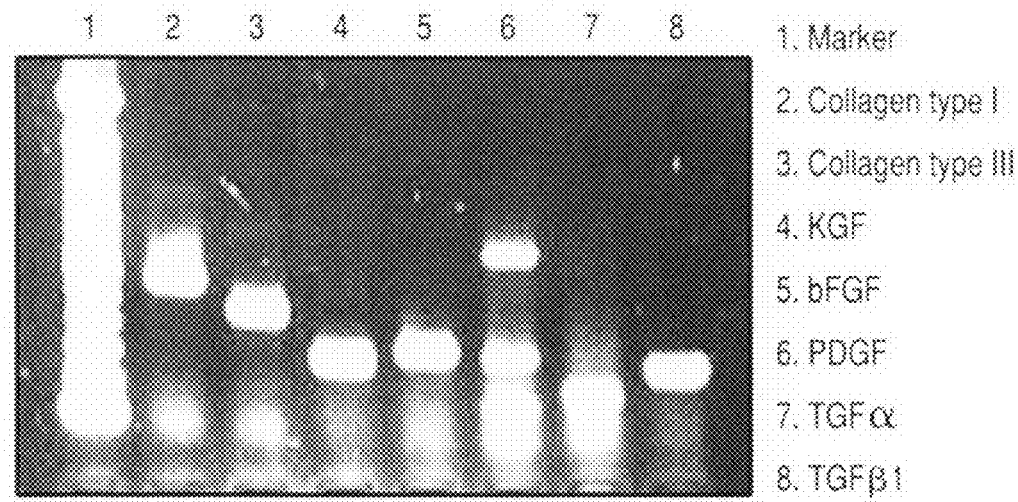
FIG. 7: Illustrates the expression of genes involved in wound healing by the cells of the tissue equivalent of the present invention.

The expression of the genes for transforming growth factor β1 (TGFβ1), keratinocyte growth factor (KGF), basic fibroblast growth factor (bFGF), transforming growth factor α (TGFα), platelet derived growth factor (PDGF), collagen type I, and collagen type III, each of which has an important role to play in the wound healing process of the skin, was determined by Reverse-Transcriptase Polymerase Chain Reaction (RT-PCR). This method detects the messenger RNA transcribed from expressed genes. The data is shown in FIG. 7. Since these genes were expressed by the tissue-equivalent, this demonstrates the capability of the three dimensional tissue equivalent of the present invention to produce wound repair.

Figure 8:
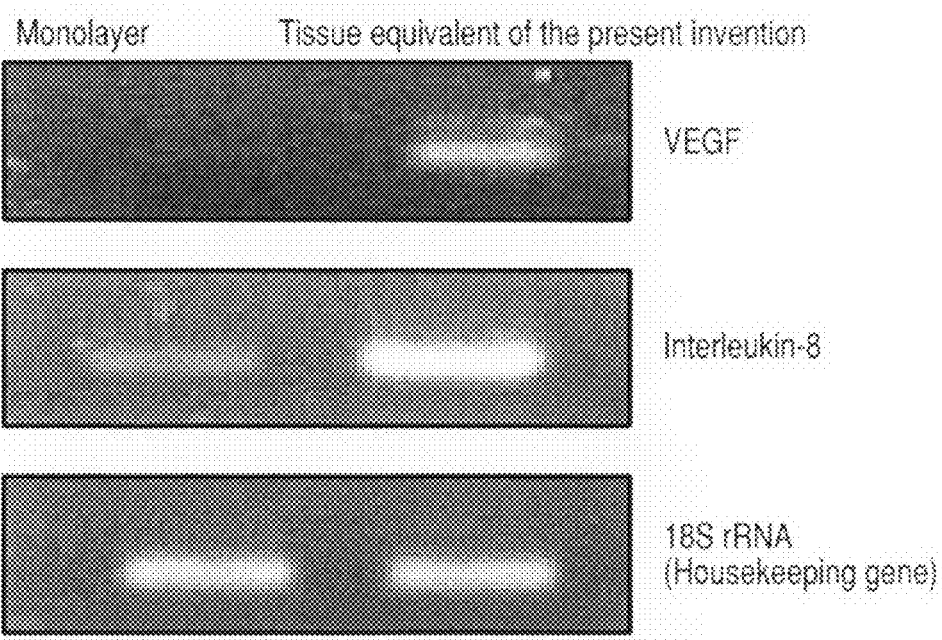
FIG. 8: Illustrates the comparison of expression of genes between tissue-equivalent of the present invention seeded with fibroblasts and fibroblast monolayers, wherein 18S rRNA expression serves as the control, the level of which is unchanged.

In addition, a comparison of the gene expression between monolayers of dermal fibroblasts and tissue equivalent of the present invention was performed by RT-PCR. It was found that the tissue equivalent of the present invention has greatly enhanced levels of VEGF and IL-8 as compared to monolayer controls. Thus, the tissue equivalent of the present invention presents dermal fibroblasts in a more desirable phenotype than simply cultured monolayers, with respect to the ability to induce angiogenesis, as mediated by VEGF, and the recruitment of neutrophils, as mediated by IL-8, to the wound bed, which would aid in clearing bacterial colonization and enhancing wound closure efficacy. This data is shown in FIG. 8, with 18S rRNA expression serving as the control, the level of which is unchanged.

VEGF is produced by cells in different isoforms, which result in VEGF proteins of different sizes and different functionality, namely VEGF206, VEGF189, VEGF165 and VEGF121. Of the VEGF forms, VEGF165 is the one that has optimal characteristics of bioavailability and biological potency. See Ferrara et. al. *Nature Med*. (2003) vol. 9, no. 6, pp. 669-676. Thus, in order to ensure that the major VEGF isoform is produced by the tissue equivalent, the RT-PCR product show in FIG. 8 was sequenced and compared to the known sequence of VEGF165 by using the "Blast 2 Sequences" program on <http://www.ncbi.nlm.nih.giv/BLAST> (October 2007). The results confirmed that the sequence indeed was of VEGF165 (data not shown).

D) Secretion of Vascular Endothelial Growth Factor

The biological activity of a gene is carried out by the protein, which is translated from the messenger RNA transcribed from the gene. Thus, it is the protein that is responsible for the biological activity. Because the VEGF165 protein induces angiogenesis, it should be secreted from the cells. In order to establish that VEGF165 is secreted from the cells of the tissue equivalent, and to quantify the amount of secreted VEGF165, the tissue equivalents of the present invention were incubated at 37° C. in culture medium for 24 hours. The culture medium was collected and VEGF 165 within the medium was detected and quantified by an Enzyme Linked Immunosorbent Assay (ELISA) using antibody specific for the VEGF165 protein form. The culture medium was positive for secreted VEGF 165 and, by quantification, it was found that a single tissue equivalent of the present invention under in vitro conditions produced about 40 ng of VEGF 165 in 24 hours after opening the package. This amount of VEGF 165 corresponds to biologically potent levels. See Mansbridge et. al. *Diabetes Obes. Metab.* (1999) 1(5):265-279.

E) Secretion of Interleukin-8

As described above for VEGF165, IL-8 protein also exerts its action after secretion from the cells. In order to establish that secreted IL-8 is produced by the tissue equivalent of the present invention and to quantify the amount, the tissue equivalent were incubated at 37° C. for 24 hours in culture medium. The culture medium was collected and secreted IL-8 within the medium was detected and quantified by ELISA. The test was positive for secreted IL-8 and it was found that a single tissue equivalent produced about 450 to 1000 ng of IL-8 in 24 hours after opening the package, under in vitro conditions. This amount of IL-8 corresponds to biologically potent levels. See Martin et. al. *Wound Rep. Reg.* (2003) 11(4):292-296.

F) Transfer of Cells to Substratum

Figure 9:
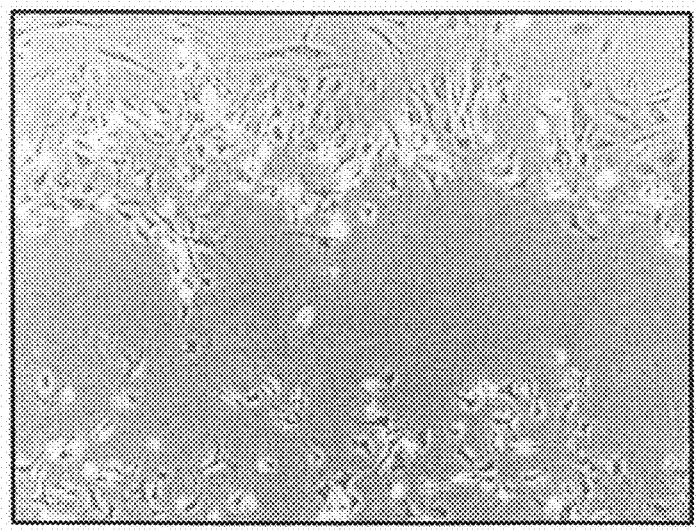
FIG. 9: Illustrates the transfer of cells to a wound bed from the tissue equivalent (substratum) after 24 hours.

In order to test the migration of the cells from the three dimensional tissue equivalent onto a substratum, the tissue equivalents were inverted and incubated on tissue culture plates in growth medium. It was found that, after 24 hours of incubation, cells had migrated to the tissue culture plates, which is shown in FIG. 9. This would contribute to the efficacy of the tissue equivalent in wound healing.

3. Purity

A) Endotoxin

Presence of bacterial endotoxins obtained from the cell wall of gram-negative bacteria is responsible for inducing high temperatures in humans. To ensure that the manufacturing process and the tissue equivalent have endotoxin below the acceptable limit, the packages were aseptically opened and the final spent transport medium was tested for endotoxins by using the gel-clot technique with the *Limulus* Amoebocyte Lysate (LAL) reagent. When incubated at 37° C. for one hour in the presence of bacterial endotoxins, the LAL reagent forms a firm gel-clot. Failure to form a gel-clot under the conditions of the test indicates absence of detectable endotoxin in the sample. The spent transport medium of the final packaged tissue equivalent of the present invention was tested to have endotoxin level <10 EU/ml. This is within the acceptable upper limit of 5 EU per kg body weight per dose (CBER guidelines, 2003), which amounts to a total of 250 EU per dose for a body weight of 50 kg.

B) Residual Protein in the Final Product

Figure 10:
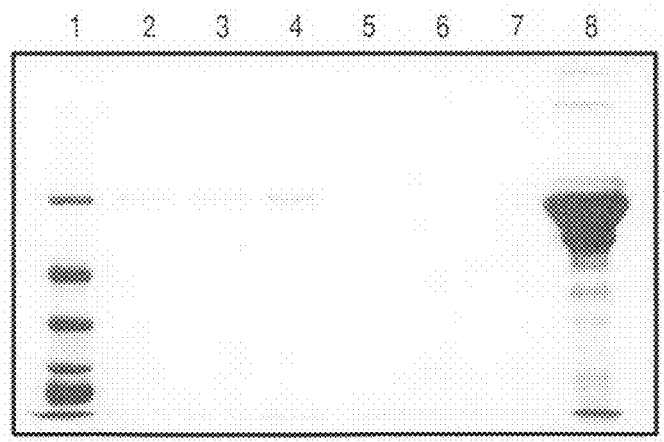
FIG. 10: Illustrates an SDS page analysis of the residual protein of the transport medium used for the tissue equivalent of the present invention.

To evaluate the level of any protein in the transport medium and the washes, the tissue equivalent of the present invention were prepared, packaged, opened and rinsed in saline. The spent transport medium and washes were collected and analyzed for presence of protein by sodium dodecyl sulphate-polyacrylamide gel electrophoresis (SDS-PAGE), followed by silver staining, which is a highly sensitive method of detecting protein in gels. The result from three batches of three-dimensional tissue equivalent is shown in FIG. 10. As can be seen, there is only a trace amount of protein in the spent transport medium, which is carried over from the upstream process, while in the first wash itself, there is no trace of any protein.

4. Stability

A) Effect of Transport Conditions on Viability

The tissue equivalent of the present invention is stored and transported in a hypothermic storage transport medium at 2-8° C. To ensure that viability is maintained at 2-8° C., batches of the tissue equivalent of the present invention were prepared, packaged, and kept at 2-8° C. for a period of 72 hours. Then the packages were opened, the tissue equivalents rinsed with saline, and the cells extracted from them. The viability of the cells was assessed using Trypan Blue vital dye and a counting chamber. Additionally, the pH of the transport medium in which the tissue equivalent of the present invention were packaged is an indication of the metabolic state of the cells while in transit. During hypothermic storage, in order for the cells remain viable, they should not metabolize. The medium pH should therefore not change. The pH would be affected if the cells had metabolized or the state of the cells was adversely altered. In this study, after opening the packages, the pH of the spent transport medium was checked. It was established that:

(i) The tissue equivalent had a viability of at least 90% after 72 hours storage at 2-8° C., which is a very high viability.

(ii) The pH of the spent transport medium was about 7.0, which indicates that the state of the cells is not adversely affected upon hypothermic storage at 2-8° C. for 72 hours.

B) Effect of the Transport Conditions on the Integrity

An important aspect of stability of a product is that the product should maintain mechanical integrity under conditions of transport and handling, during which there is agitation and impact. Therefore, a simulated study was carried out in which batches of the tissue equivalent were placed in a transport box and then subjected to continuous agitation for two periods of about 2 hours and also subjected to impact. The box was then opened and the tissue equivalents were assessed for maintenance of mechanical integrity by observing whether they were broken or torn. It was established that there was no loss of integrity of the tissue equivalent and no alteration in shape.

Example 3

In Vivo Studies and Toxicology

1. Study of Efficacy and Safety of Tissue Equivalent of the Present Invention in a Wound Healing Animal Model.

The efficacy and safety of the tissue equivalent of the present invention was assessed by performing a skin wound healing study in severe combined immunodeficient (SCID) CB17 mice. SCID mice were used since the dermal dressing to be tested consists of human cells, which would undergo xenograft rejection if tested on animals that are non-immunocompromised. The study was carried out in accordance with CPCSEA guidelines and with IAEC approval. There were four sets of animals, one set for each time period after surgery and application where tissue would be harvested, namely, 4 days, 8 days, 12 days, and 16 days. For each time point, there were three control animals and six animals treated with the tissue equivalent. In the control group, chitosan sponge alone was applied on each wound. In the treated group, the tissue equivalent was applied on each wound, with the cellular sheet side facing the wound bed. Animals were anaesthetized and surgery was performed in a laminar flow workstation. A single full-thickness wound of 6 mm diameter was created on the back of each animal, using a punch biopsy instrument. After application of tissue equivalent or chitosan sponge alone, the wounds were dressed with bandage. The animals were observed for the above mentioned time points. At the end of each time point, animals were sacrificed and skin tissue was obtained from the wound healing area of each animal. The tissues were fixed and analyzed histologically with respect to various parameters.

The main observations from the preclinical evaluation were:
(i) Faster rate of complete epithelization in treated animals compared to control animals.
(ii) Earlier angiogenic response or neovascularization in treated animals compared to control animals.
(iii) Earlier formation of new extracellular matrix (ECM) in treated animals compared to control animals.
(iv) Enhanced accumulation of polymorphonuclear leucocytes (PMN) in treated animals compared to control animals.
(v) There was no foreign body reaction (foreign body giant cells) in either treated or control animals.
(vi) The chitosan sponge was not integrated into the skin after complete wound closure, either in treated or control animals.
(vii) There were no adverse events seen in either treated or control animals, such as, oedema, erythema, or fluid collection.

Figure 11:
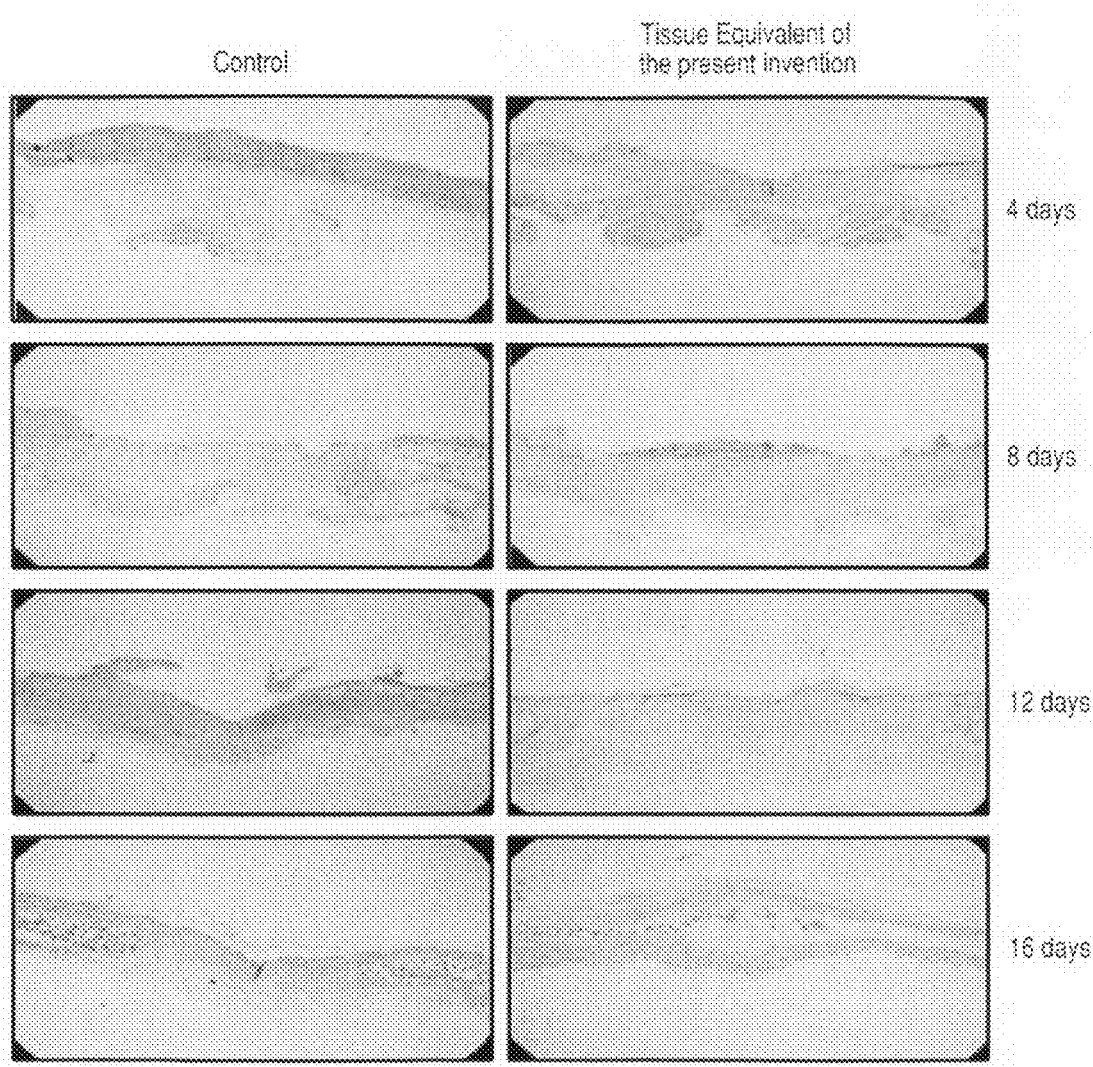
FIG. 11: Illustrates a preclinical study of efficacy and safety of the three dimensional tissue equivalent of the present invention in a wound healing animal model, wherein selected photographs of the histological sections (haematoxylin and eosin staining) through the wound healing area at different time points are depicted.

Details of the data are summarized in Table 1, and selected photographs of the histological sections (haematoxylin & eosin staining) through wound healing area at different time points are depicted in FIG. 11. Thus, the studies proves that application of the tissue equivalent of the present invention enhanced the healing of full-thickness wounds in SCID mice, compared to control animals, and has shown no adverse affects.

TABLE 1

| Parameter/Timepoint | 4 days | | 8 days | | 12 days | | 16 days | |
| --- | --- | --- | --- | --- | --- | --- | --- | --- |
| | Control | Treated with tissue equivalent | Control | Treated with tissue equivalent | Control | Treated with tissue equivalent | Control | Treated with tissue equivalent |
| Neo-vascularization | 0% | 60% | 66% | 83% | 100% | 83% | 100% | 100% |
| PMN > 10 per 20× field | 100% | 100% | 100% | 100% | 0% | 66% | 0% | 0% |
| New ECM formation | 0% | 80% | 100% | 100% | 100% | 100% | 100% | 100% |
| Epithelization | | | | | | | | |
| 3 mm or less gap | 0% | 20% | 0% | 66% | 100% | 100% | 100% | 100% |
| 1 mm or less gap | 0% | 0% | 0% | 16% | 0% | 83% | 100% | 100% |
| 0 mm gap | 0% | 0% | 0% | 0% | 0% | 50% | 100% | 100% |

The values given for each parameter is the percentage of animals positive for that parameter in each group. Percentage increase of 50% or greater in treated animals over control animals is underlined. In the Epithelization parameter, there are 3 categories, viz., gap remaining for complete epithelization 3 mm or less, 1 mm or less, and 0 mm (ie complete epithelization). PMN=Polymorphonuclear leucocytes; ECM=Extracellular matrix. Foreign body reaction: Not seen in any animal.

Integration of sponge into skin: Not seen in any animal. Other adverse events: Not seen in any animal (eg. oedema, erythema, fluid collection).

2. Toxicology

A) Safety of the Three Dimensional Tissue Equivalent

As described earlier, the safety of the three dimensional tissue equivalent of the present invention upon application on full-thickness wounds in mice has been confirmed, with no signs of reactivity (oedema, erythema, fluid collection) upon intracutaneous application in the full-thickness wounds created on the animals.

B) In Vivo Tumorigenicity of the Three Dimensional Tissue Equivalent

The in vivo tumorigenic potential of cells from the three dimensional tissue equivalent of the present invention on a dermal wound dressing was studied with IAEC approval by injecting end-of-production stage fibroblasts extracted from the tissue equivalent into SCID CB17 mice. A total of $1\times10^6$ cells (98% cell viability), suspended in 50 µl of sterile normal saline, was injected (i.m.) in the left hind limb of each of six SCID CB17 mice. The mice were observed for three months.

There were no tumors developed and it was concluded that cells from the tissue equivalent of the present invention are non-tumorigenic.

C) Ames Mutagenicity

In order to assess if the spent transport medium of the tissue equivalent has mutagenic property, *Salmonella typhimurium* Reverse Mutation Assay, Test no. 471 was conducted according to the OECD Principles of Good Laboratory Practice (1982). The tissue equivalent of the present invention was prepared, packaged and kept at 2-8° C. for 72 hours. The packages were then opened and the spent transport medium collected and tested as per the above mentioned assay. The spent transport medium was tested at the concentrations of 61.72, 185.18, 555.55, 1666.67 and 5000 µg/plate using sterile distilled water as solvent. The study was performed without and with metabolic activation (S9 fraction) prepared from sodium phenobarbital induced rat liver. The solvent control and appropriate positive controls were tested simultaneously. Plating was done in triplicate for each concentration of test substance. The study showed that the mean numbers of revertant colonies counted at different concentrations of test substance were comparable to that of the controls, in the absence and presence of metabolic activation. The number of revertant colonies in the positive controls increased by 3.93 to 95.33 fold under identical conditions.

Hence the spent transport medium tested at 61.72, 185.18, 555.55, 1666.67 and 5000 µg/plate did not induce mutations in *Salmonella typhimurium* up to the maximum concentration of 5000 µg/plate.

D) Hemolysis of Red Blood Cells

The spent transport medium of the tissue equivalent was evaluated for hemolytic activity by using freshly collected heparinized rabbit blood. Heparinized rabbit blood was added to each of negative control, positive control, and undiluted test spent medium in triplicate. The samples were mixed and incubated at 37° C. for 1 hour. They were then centrifuged at 3500 rpm for 5 minutes. The absorbance of the supernatants was measured at 545 nm. The percent hemolysis shown by the spent transport medium of tissue equivalent of the present invention was 0.38%, which is less than the acceptable limit of 5%; hence the transport medium was non-hemolytic.

E) Cytotoxicity

Figure 12:
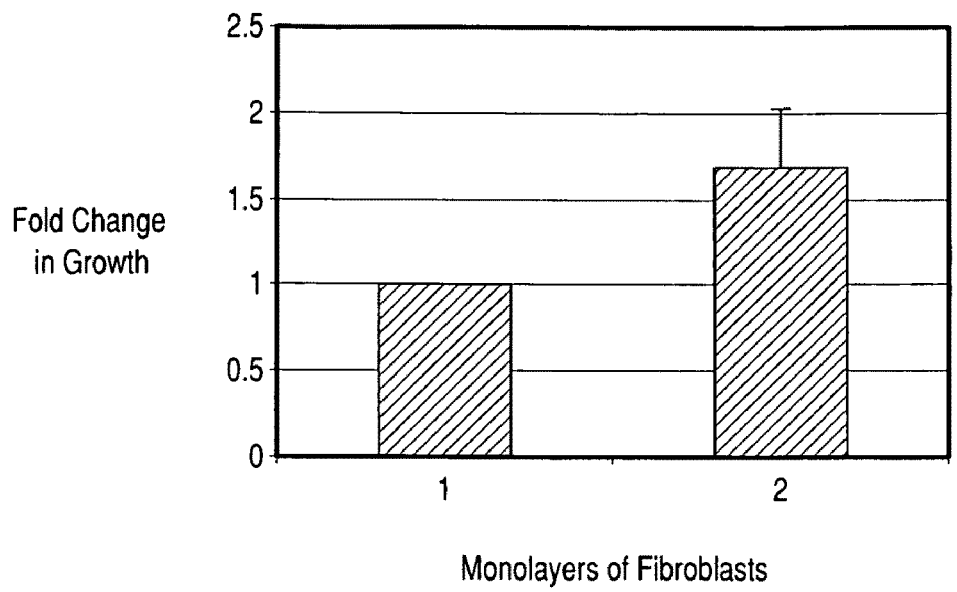
FIG. 12: Illustrates the result of a test for cytotoxicity to show that the tissue equivalent of the present invention is not cytotoxic to fibroblasts. (1) illustrates the test without the tissue equivalent of the present invention, and (2) illustrates the test with the tissue equivalent of the present invention.

The cytotoxicity of the tissue equivalent of the present invention was studied by measuring its effect on the growth of monolayers of dermal fibroblasts. This type of measurement was taken as an indication of cytotoxicity, since dermal fibroblasts are important cells in the wound bed of non-healing ulcers and on which tissue equivalent of the present invention is to be applied. Equal numbers of fibroblasts as monolayers were incubated by themselves or in the presence of tissue equivalent of the present invention by placing them in cell culture inserts over the monolayers. Growth of the fibroblast monolayers was assessed after 48 hours by MTT staining, which was quantified by measuring absorbance at 570 nm. The growth of fibroblast monolayers in the absence of tissue equivalent of the present invention was taken as 100%, i.e., a fold change of 1.0 in growth. The result of the cytotoxicity assay is shown in FIG. 12. It was observed that the growth of fibroblast monolayers did not decrease or appear adversely affected when incubated in the presence of tissue equivalent of the present invention, as compared to without it. Rather, there was an increase in growth of fibroblasts, when incubated in the presence of tissue equivalent of the present invention. Hence the tissue equivalent of the present invention was non toxic towards cells namely dermal fibroblasts.

Example 4

Use of the Tissue-Equivalent of the Present Invention for In Vitro Purposes

1. As an In Vitro Model for Drug Testing

Figure 13:
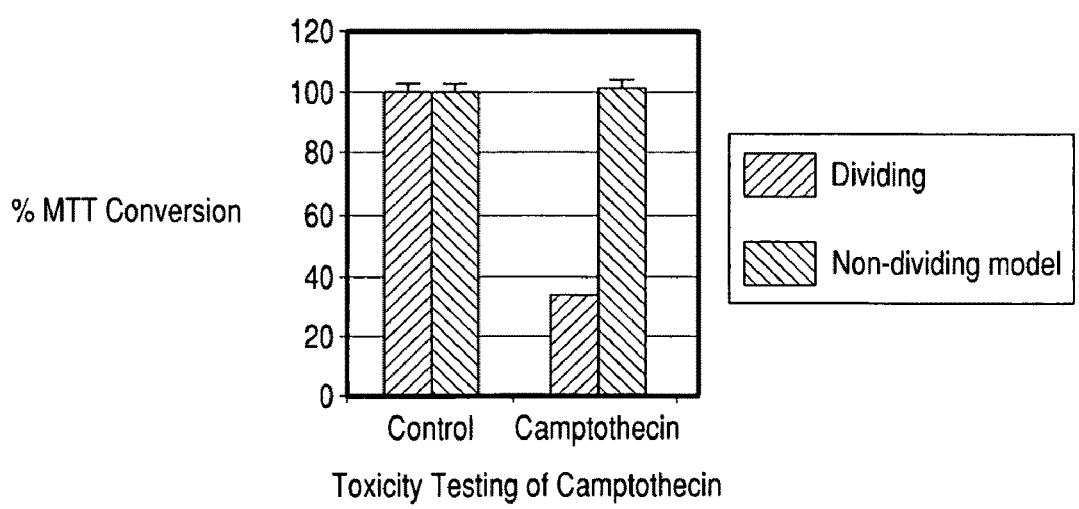
FIG. 13: Illustrates an in vitro use of the three dimensional tissue equivalent of the present invention in toxicity testing of chemicals. "Dividing" indicates monolayers of fibroblasts and "Non-dividing model" indicates the tissue equivalents.

As mentioned previously, the tissue equivalent of the present invention could be used as an in vitro model of normal non-dividing cells for safety testing of anti-cancer compounds. To test its usefulness as such a model, dividing monolayers of fibroblasts and the tissue-equivalent of the present invention were incubated with or without (control) camptothecin, an anti-cancer drug known to act on dividing cells and not on non-dividing cells. Both were incubated for the same period of time. Then the metabolic activity was assessed by incubating both groups in MTT, which was quantified by spectrophotometry. FIG. 13 shows the results. It was found that camptothecin was toxic to the actively dividing monolayer cells, while it showed no toxicity towards the tissue-equivalent of the present invention. This showed that the tissue-equivalent of the present invention contains the cells in a non-dividing state, since if any cells were present in S-phase, they would have been destroyed by camptothecin. Leroy et al. *Ann. N.Y. Acad. Sci.* (2000) 922:1-10. Thus, these are normal cells in a non-dividing state, which could be a model of the normal quiescent cells of the human body, in contrast to the abnormal tumour cells which are rapidly dividing. Thus, it demonstrated that the tissue-equivalent of the present invention has potential for in vitro use, for example, in the safety testing of anti-cancer drugs whose mode of action is to destroy actively dividing cells.

2. For Production of Proteins

As described above in the examples, the tissue-equivalent of the present invention has highly enhanced expression of VEGF and IL-8, a single tissue equivalent secreting about 40 ng of VEGF and 450-1000 ng of IL-8 in 24 hours. Thus, the tissue equivalent is a good in vitro factory for producing these proteins.

Based on the foregoing description, specific embodiments of the present invention have been disclosed. It is apparent that various modifications and substitutions could be made to the present invention, which would not be departures from the central concept of the present invention. The present invention provides a method for temporarily filling or blocking the pores of a porous matrix with a substance that can be maintained in a solid or semi-solid state, thereby not allowing cells seeded to form a cellular sheet on one side of the matrix to pass through, and also allows for later removal of the blocking substance from the pores of the porous matrix. Examples of modifications or substitutions include the use of different blocking substances, the use of methods other than temperature variation for blocking and unblocking, the use of different concentrations of blocking substance, the use of different experimental systems or designs, and the use of different methods for blocking and unblocking pores based on the properties of the blocking substance. Likewise, sheet formation over a support should be possible at other higher densities than mentioned here. A person with skill in the art can easily devise adaptations of the present method, based on the above central theme. Therefore, although only the described embodiments have been brought forth, they serve the purpose of example or illustration only and should not be construed as limiting the present invention.

The invention claimed is:

1. A process for preparing a three dimensional non-contractile tissue equivalent comprising a macromass cellular sheet of dermal fibroblast cells adhered to a porous scaffold or matrix, wherein the method comprises:
   a) absorbing a liquid blocking agent into pores of the porous scaffold or matrix,
   b) solidifying the blocking agent;
   c) culturing dermal fibroblast cells onto only one side of the porous scaffold or matrix to form a multilayered high density macromass cellular sheet, wherein the porous scaffold or matrix comprises pores that do not contact the macromass cellular sheet and are devoid of the cells;

d) desolidifying and removing the blocking agent; and e) forming a three dimensional non-contractile tissue equivalent comprising the macromass cellular sheet adhered to the porous scaffold or matrix.

2. The method of claim 1, wherein the dermal fibroblast cells comprise neonatal human dermal fibroblast cells.

3. The method of claim 1, wherein the blocking agent comprises material chosen from gelatin, alginate, pectin, agar and agarose.

4. The method of claim 1, wherein the porous scaffold or matrix comprises material chosen from chitosan, collagen, polyglycolic acid, and polylactic acid.

5. The method of claim 1, wherein the dermal fibroblast cells do not leak or pass through the pores of the porous scaffold or matrix during the culturing step.

6. The method of claim 1, wherein at least $20 \times 10^6$ dermal fibroblast cells are seeded onto the porous scaffold or matrix during the culturing step, and wherein the macromass cellular sheet has a cell density of $1 \times 10^6$ cells per $cm^2$ to $12 \times 10^6$ cells per $cm^2$ of the porous scaffold or matrix.

7. The method of claim 1, wherein the cells in the macromass cellular sheet express VEGF and/or IL-8 in an amount greater than would be expressed by the same cells in a monolayer having the same diameter as the macromass cellular sheet.

* * * * *